United States Patent
Pan et al.

(10) Patent No.: US 10,466,106 B2
(45) Date of Patent: Nov. 5, 2019

(54) GAS CONCENTRATION MEASUREMENT BY 2F SIGNAL TROUGH DISTANCE

(71) Applicant: NEC Laboratories America, Inc., Princeton, NJ (US)

(72) Inventors: Da Pan, Jersey City, NJ (US); Yue Tian, Princeton, NJ (US); Ming-Fang Huang, Princeton, NJ (US)

(73) Assignee: NEC Corporation (JP)

( * ) Notice: Subject to any disclaimer, the term of this patent is extended or adjusted under 35 U.S.C. 154(b) by 0 days.

(21) Appl. No.: 16/219,136

(22) Filed: Dec. 13, 2018

(65) Prior Publication Data

US 2019/0195789 A1 Jun. 27, 2019

Related U.S. Application Data

(60) Provisional application No. 62/609,506, filed on Dec. 22, 2017.

(51) Int. Cl.
*G01J 3/433* (2006.01)
*G01N 21/39* (2006.01)
*G01N 21/27* (2006.01)

(52) U.S. Cl.
CPC .............. *G01J 3/433* (2013.01); *G01J 3/4338* (2013.01); *G01N 21/274* (2013.01); *G01N 21/39* (2013.01); *G01N 2021/399* (2013.01); *G01N 2201/127* (2013.01)

(58) Field of Classification Search
CPC ...... G01N 21/25; G01N 21/27; G01N 21/274; G01N 21/31; G01N 21/35; G01N 21/3504; G01N 21/39; G01N 2021/399; G01N 2201/12; G01N 2201/121; G01N 2201/1215; G01N 2201/127; G01N 2201/12715; G01N 2201/1273; G01N 2201/12746; G01N 2201/12753; G01N 2201/12784; G01N 2201/12792; G01J 3/42; G01J 3/433; G01J 3/4338; G01J 2003/4332; G01J 2003/4334

See application file for complete search history.

(56) References Cited

U.S. PATENT DOCUMENTS

| | | | | |
|---|---|---|---|---|
| 5,436,459 A * | 7/1995 | Koch | ...................... | G01N 21/39 250/373 |
| 5,448,071 A * | 9/1995 | McCaul | ............... | G01N 21/274 250/343 |
| 6,940,599 B1 * | 9/2005 | Hovde | ..................... | G01J 3/433 250/343 |
| 7,957,001 B2 | 6/2011 | Liu et al. | | |

(Continued)

FOREIGN PATENT DOCUMENTS

WO WO-2018223107 A1 * 12/2018

*Primary Examiner* — Gordon J Stock, Jr.
(74) *Attorney, Agent, or Firm* — Joseph Kolodka

(57) ABSTRACT

A computer-implemented method for measuring gas concentration from a 2f signal in wavelength modulation spectroscopy is presented. The computer-implemented method includes emitting a beam of light from a laser to pass through a gas sample, calculating a gas measurement value from the gas sample via a trough distance calculator using a trough distance of a gas absorption line's 2f signal, calibrating the gas measurement value via a multi-point calibration process, and outputting the gas measurement value to a user interface of a computing device.

14 Claims, 10 Drawing Sheets

(56) References Cited

U.S. PATENT DOCUMENTS

| | | | |
|---|---|---|---|
| 8,094,313 B2* | 1/2012 | Kluczynski | G01J 3/4338 |
| | | | 356/437 |
| 8,896,835 B2* | 11/2014 | Ido | G01N 21/59 |
| | | | 356/432 |
| 9,810,627 B2 | 11/2017 | Huang et al. | |
| 10,234,378 B2* | 3/2019 | Alizadeh | G01N 21/274 |
| 2006/0262901 A1* | 11/2006 | Heaton | G01V 5/0033 |
| | | | 378/57 |
| 2009/0001262 A1* | 1/2009 | Visser | G06K 9/6242 |
| | | | 250/282 |
| 2012/0283961 A1* | 11/2012 | Wittmann | G01N 21/39 |
| | | | 702/24 |
| 2014/0067282 A1* | 3/2014 | Beyer | G01N 21/3504 |
| | | | 702/24 |
| 2014/0340684 A1* | 11/2014 | Edler | G01J 3/4338 |
| | | | 356/409 |
| 2016/0047739 A1* | 2/2016 | Bitter | G01N 21/31 |
| | | | 356/402 |

* cited by examiner

GAS CONCENTRATION MEASUREMENT BY 2F SIGNAL TROUGH DISTANCE

This application claims priority to Provisional Application No. 62/609,506, filed on Dec. 22, 2017, the contents of which are incorporated herein by reference in their entirety.

BACKGROUND

Technical Field

The present invention relates to gas sensing and, more particularly, to gas concentration measurements by employing 2f signal trough distance.

Description of the Related Art

Trace gas sensing plays a role in many industrial and environmental applications. Gas concentration levels around a facility can inform the owner if the tools and machinery in the facility are functioning properly. Gas concentration level information can also assist in preventing environmental damage by showing that changes need to be made before gas concentrations reach harmful or dangerous levels. In certain conditions (such as dealing with dangerous chemicals or volcanoes), the detection location may be too inaccessible or dangerous for human beings to install gas sensing equipment. This makes the gas measurement particularly difficult.

SUMMARY

A computer-implemented method for measuring gas concentration from a 2f signal in wavelength modulation spectroscopy is presented. The method includes emitting a beam of light from a laser to pass through a gas sample, calculating a gas measurement value from the gas sample via a trough distance calculator using a trough distance of a gas absorption line's 2f signal, calibrating the gas measurement value via a multi-point calibration process, and outputting the gas measurement value to a user interface of a computing device.

A non-transitory computer-readable storage medium comprising a computer-readable program is presented for measuring gas concentration from a 2f signal in wavelength modulation spectroscopy, wherein the computer-readable program when executed on a computer causes the computer to perform the steps of emitting a beam of light from a laser to pass through a gas sample, calculating a gas measurement value from the gas sample via a trough distance calculator using a trough distance of a gas absorption line's 2f signal, calibrating the gas measurement value via a multi-point calibration process, and outputting the gas measurement value to a user interface of a computing device.

A system for measuring gas concentration from a 2f signal in wavelength modulation spectroscopy is presented. The system includes a laser to emit a beam of light to pass through a gas sample, a gas measurement value calculated from the gas sample via a trough distance calculator using a trough distance of a gas absorption line's 2f signal, a multi-point calibration module to calibrate the gas measurement value, and a user interface of a computing device to output the gas measurement value.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The exemplary embodiments of the present invention calculate gas concentration from trough distance in a much larger dynamic range. The trough distance of the gas absorption line's 2f signal always increases with the gas concentration, even when the optical absorption is saturated. By linear fitting and/or multi-point calibration, the gas concentration can be calculated. Thus, the exemplary embodiments of the present invention can calculate gas concentration from 2f signal in wavelength-modulation spectroscopy (WMS) even when the gas concentration is high enough to saturate the optical absorption, by employing the trough distance of the gas absorption line's 2f signal.

Wavelength-modulation spectroscopy has become the mainstream technology of laser-based gas analyzers. In wavelength-modulation spectroscopy, a laser is wavelength-modulated at a certain frequency, 1f, passes through a sample, and the transmission coefficient of the sample is demodulated by phase-sensitive detection at a certain harmonic of modulation frequency to produce a harmonic spectrum. Predominantly, the second harmonic, 2f, is chosen for demodulation frequency. Phase-sensitive detection is an effective noise reduction technique and has made wavelength-modulation spectroscopy a highly sensitive method. The harmonic spectral signal magnitude reflects the concentration of an absorbing analyte in the sample. Specifically for 2f, the peak height of a 2f spectrum is linear with the analyte concentration within a certain range. Such linearity is the foundation of present 2f gas analyzers.

Wavelength-modulation spectroscopy traditionally is transmission-based, i.e., a harmonic spectrum is generated by demodulating the transmission coefficient of the sample. Because it is transmission-based, the harmonic spectral signal magnitude is inherently nonlinear with the analyte concentration, and can be considered linear with the analyte concentration only when the concentration is so low that absorbance is less than 0.05. Consequently, a gas analyzer utilizing wavelength-modulation spectroscopy has a narrow dynamic range, usually less than two decades ($10^2$). Beyond the dynamic range, the harmonic spectral signal magnitude is nonlinear with the analyte concentration. As such, the exemplary embodiments of the present invention employ a 2f signal trough distance to calculate gas concentration. The 2f signal trough distance can further be employed to indicate or determine optical absorption strength.

Figure 1:
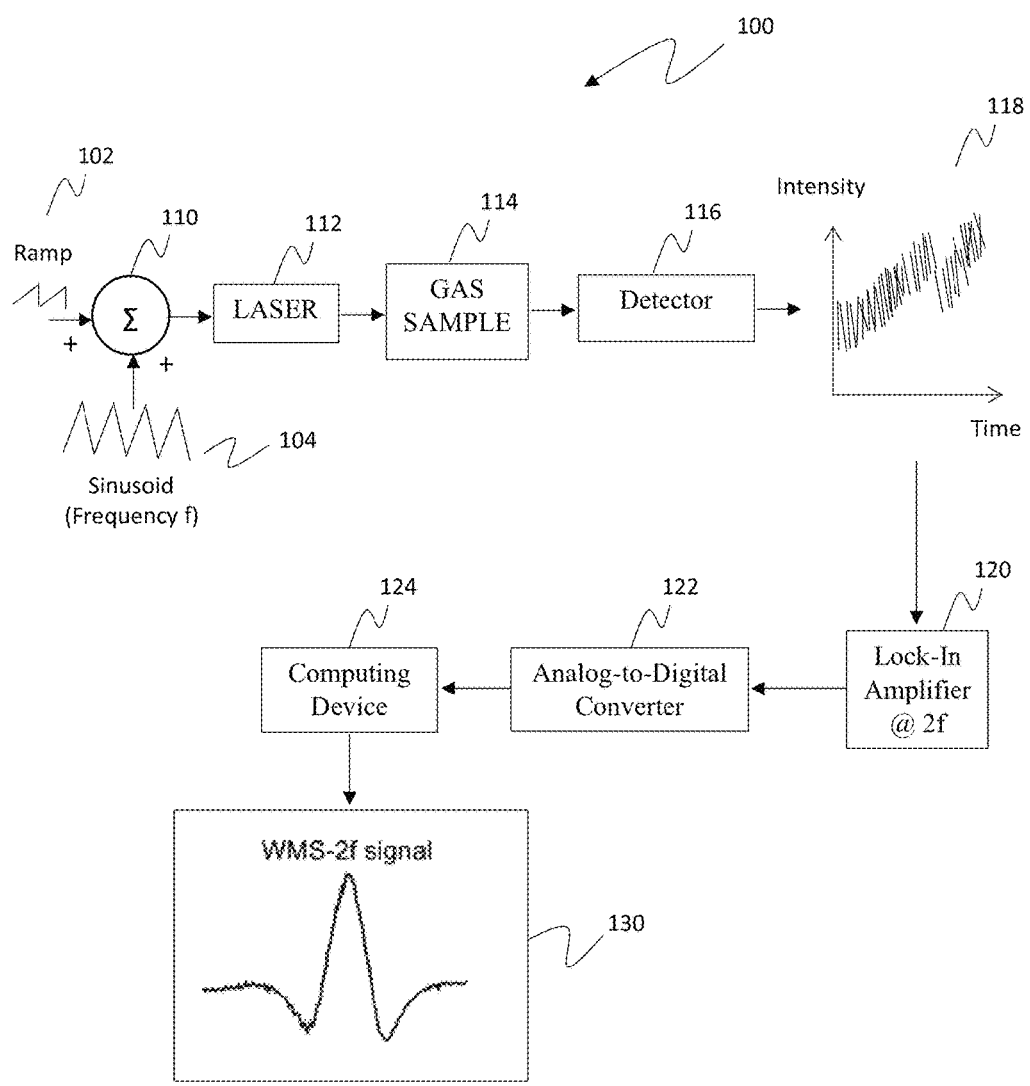
FIG. 1 is an example wavelength modulation spectroscopy system, in accordance with embodiments of the present invention.

FIG. 1 is an example wavelength modulation spectroscopy system 100, in accordance with embodiments of the present invention.

Wavelength-modulation spectroscopy (WMS) is similar to direct-absorption spectroscopy, except the laser wavelength is additionally modulated with a rapid sinusoid (at frequency f). The interaction between the rapidly modulating wavelength and a nonlinear absorption feature gives rise to harmonic components in the detector signal, which can be isolated with lock-in amplifiers. Generally, the second harmonic (2f) is used because like direct absorption, the 2f signal is strongly dependent on spectral parameters and gas properties and can therefore be compared with spectral simulations to infer gas properties. In addition to its sensitivity to gas properties, however, WMS-2f has several benefits which make it desirable over direct absorption for certain sensing applications. The 2f signal is sensitive to spectral shape or curvature rather than absolute absorption levels, which is useful for certain high-density spectra, particularly those that are affected by broadband absorption or emission. Also, the use of a lock-in amplifier serves to reject noise that falls outside of the lock-in pass band, such as laser intensity and electronic noise.

For laser sources that have synchronous tuning of the laser wavelength and intensity (such as diode lasers), the intensity modulation is usually the strongest component of the first harmonic (1f) signal, and can be used to normalize the 2f signal against perturbations to the laser intensity by laser drift, window fouling, beam steering, or scattering. This attribute of WMS is particularly useful in harsh environments.

FIG. 1 shows a schematic of a scanned-wavelength WMS measurement using a diode laser. Much like traditional scanned-wavelength direct-absorption measurements, the diode-laser injection current is tuned with a repetitive ramp waveform. This has the effect of repetitively ramping the laser intensity and the laser wavelength across the absorption feature. Unlike traditional direct absorption, however, an additional high-frequency sinusoid is superimposed on the repetitive injection-current ramp to generate an additional high-frequency modulation in both the laser intensity and wavelength. When the laser wavelength is tuned across an absorption feature (e.g. by the repetitive ramp), the high-frequency wavelength modulation causes the laser to scan back-and-forth over part of the absorption feature twice per modulation cycle. Absorption thus affects the shape of the transmitted laser intensity and introduces harmonic components to the detected signal.

The detector signal is passed to several digital lock-in amplifiers to isolate the 2f signals. The lock-in amplifiers act by multiplying the detector signal by a reference sinusoid at the frequency of interest (2f) to take advantage of the trigonometric identity, $\cos(\alpha)\cos(\beta)=\frac{1}{2}\cos(\alpha-\beta)+\frac{1}{2}\cos(\alpha+\beta)$, to shift the harmonic components at the frequency of interest to DC. A low-pass filter is then applied to isolate the DC value and eliminate all components outside of the filter bandwidth.

In particular, with reference to FIG. 1, a summer 110 receives carrier signal 104 and the modulating signal 102. The carrier signal 104 can be, e.g., a sinusoidal waveform and the modulating signal 104 can be, e.g., a ramp waveform. The laser 112 is tuned with signals 102, 104. The laser 112 emits a light or a beam of light onto or through a gas sample 114. Light emitted from robust, tunable diode sources 112 is passed through a gaseous test sample 114 to a detector 116, and the absorption of light can be related to gas temperature, pressure, species concentration, and velocity using spectral absorption models for the target absorbing species.

The laser 112 is tuned across the feature and results in a detector signal similar to the one shown (intensity vs. time graph 118). The interaction between the rapidly modulating wavelength and a nonlinear absorption feature gives rise to harmonic components in the detector signal, which can be isolated with lock-in amplifiers 120. The data signals can be provided to an analog to digital converter 122 that displays the data 130 on a user interface of a computing device 124. The data 130 can be, e.g., a WMS-2f signal.

Moreover, the light sources 112 can include different sources of light depending on the target gases. In one embodiment, the light sources 112 can include light emitting diodes (LEDs), lasers, ultraviolet (UV) lamps, etc. The LED can be employed for $O_2$ (oxygen), $O_3$ (ozone), $H_2O$, $NO_x$ detection. In another embodiment, the light sources 112 can include a distributed feed-back laser diode (DFB-LD). The distributed feed-back laser diode (DFB-LD) can be employed for CO, $CO_2$, $N_{20}$ (nitrous oxide), NO (nitrix oxide), $CH_4$ (methane), HI (hydrogen iodide), HBr (hydrogen bromide), HF (hydrogen fluoride), HCl (hydrogen chloride), $C_2H_2$ (acetylene), HCN (hydrogen cyanide), $H_2S$ (hydrogen sulfide), $NH^3$ (ammonia), $H_2CO$ (formaldehyde) measurements using the appropriate wavelength of light. In another embodiment, the light sources 112 can include a quantum cascaded laser (QCL), which can be used for HBr, HCl, $C_2H_2$, $C_2H_6$ (ethane), $CH_4$, $N_2O$, $NO_2$, NO, $CO_2$, CO, $SO_2$ (sulfur dioxide), HCN, $NH^3$, $H_2CO$, $PH^3$ (phosphine), $O_2$ sensing using the appropriate wavelength of light. In another embodiment, the light sources 112 can include ultraviolet (UV) lamps, which may be used for NOx, $SO_2$, $O_3$ sensing.

Figure 2:
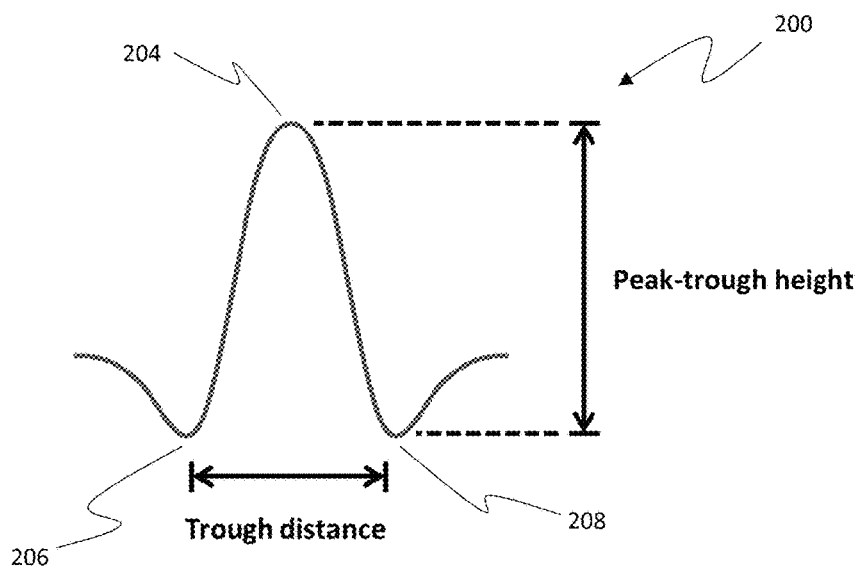
FIG. 2 is an example gas absorption line 2f signal, in accordance with embodiments of the present invention.

FIG. 2 is an example gas absorption line 2f signal, in accordance with embodiments of the present invention.

Gas absorption line's 2f signal is shown in FIG. 2, when the gas concentration is low and optical absorption is not saturated. The definitions of peak-trough height and trough distance are also illustrated in FIG. 2. The 2f signal 200 has a peak 204 and two troughs 206, 208.

Figure 3:
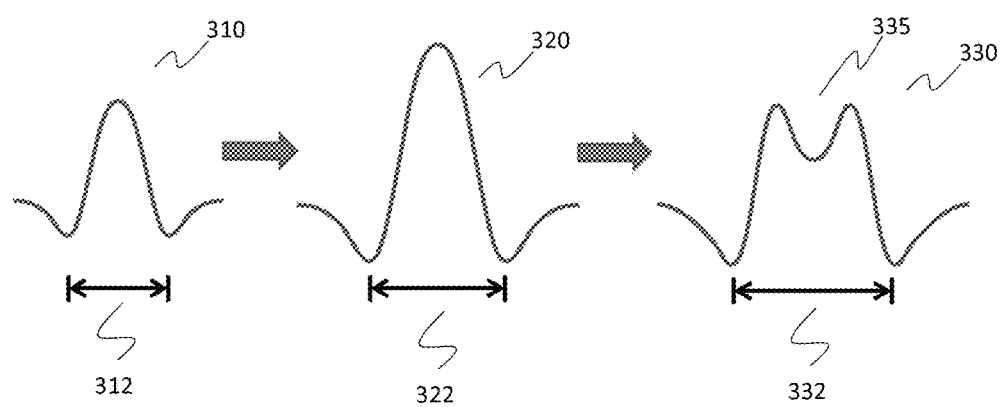
FIG. 3 illustrates how the gas absorption line 2f signal of FIG. 2 changes as the gas concentration steadily increases, in accordance with embodiments of the present invention.

FIG. 3 illustrates how the gas absorption line 2f signal of FIG. 2 changes as the gas concentration steadily increases, in accordance with embodiments of the present invention.

When the gas concentration increases, the 2f signal shape changes accordingly. Firstly, as shown in 310, as the optical absorption becomes stronger, both the peak-trough height and trough distance 312 increase, approximately linearly with gas concentration. Then, when the gas concentration further increases, as shown in 320, the peak-trough height increases nonlinearly with gas concentration. However, the trough distance 322 further increases. Finally, if the gas concentration continues to increase, as shown in 330, the optical absorption begins to saturate and the 2f signal shape gets distorted as shown on the right in FIG. 3. The central part of the peak of the 2f signal begins to decrease as the gas concentration further increases and the 2f signal shows two "shoulders" 335 higher than the center. In this case, the peak-trough height no longer increases with gas concentration, but decreases instead. However, the trough distance 332 continues to increase. As a result, high gas concentration values cannot be calculated by measuring 2f signal peak-trough height in this case. In contrast, the trough distance 312, 322, 332 of the 2f signal is constantly increasing linearly with gas concentration. Therefore, by using trough distance or by combining trough distance and peak-trough height, very high gas concentration values can also be calculated. The dynamic range can be increased dramatically compared to using peak-trough height alone in conventional wavelength modulation spectroscopy (WMS). In addition, 2f signal trough distance also can be used to indicate the optical absorption strength of the 2f signal.

Figure 4:
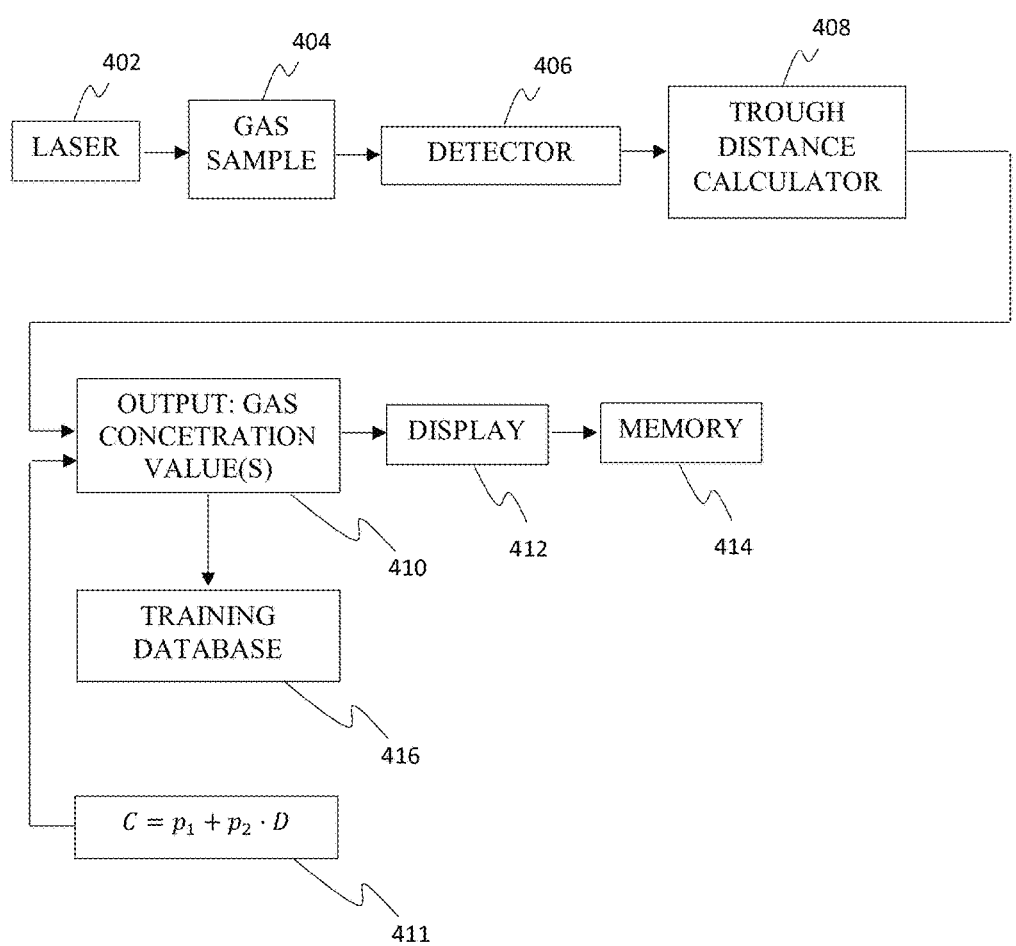
FIG. 4 is an example system for calculating gas concentration values by employing a trough distance calculator, in accordance with embodiments of the present invention.

FIG. 4 is an example system for calculating gas concentration values by employing a trough distance calculator, in accordance with embodiments of the present invention.

Light emitted from robust, tunable diode sources 402 is passed through a gaseous test sample 404 to a detector 406, and the absorption of light can be related to gas temperature, pressure, species concentration, and velocity using spectral absorption models for the target absorbing species. In some cases, a trough distance calculator 408 is employed after the detector 406. The trough distance calculator 408 can be a software component.

The multi-point calibration process involves determining coefficients $p_1$ and $p_2$ by measuring D at different known concentration C.

The trough distance calculator 408 can determine a distance between the troughs.

The gas concentration values 410 can be computed and displayed on a display 412 and stored in a memory 414. The gas concentration values 410 can also be provided to a training database 416, as described in further detail below.

Therefore, in FIG. 4, only trough distance (D) can be employed to calculate gas concentration (C). Gas concentration C is a linear function of trough distance D, given by the equation 411: $C = p_1 + p_2 \cdot D$. The multi-point calibration process involves determining coefficients $p_1$ and $p_2$ by measuring D at different known concentration C. As a result, in use, unknown concentration C can be calculated by measuring D and the equation 411: $C = p_1 + p_2 \cdot D$.

Moreover, the 2f signal trough distance is further employed to determine optical absorption strength of the 2f signal.

Regarding the training database 416, machine learning techniques can be employed.

As a broad subfield of artificial intelligence, machine learning is concerned with the design and development of algorithms and techniques that allow computers to "learn."

At a general level, there are two types of learning: inductive and deductive. Inductive machine learning methods extract rules and patterns out of massive data sets. The major focus of machine learning research is to extract information from data automatically by computational and statistical methods, hence, machine learning is closely related to data mining and statistics. Embodiments of machine learning can appear in "supervised adaption" and "adaption of algorithms" to evaluate or determine or assess gas emissions or levels or concentrations from a plurality of sources in a plurality of different environments.

Machine learning techniques are more effective as compared with the statistical techniques to detect and analyze events in time-series data. This is because machine learning has two important features, that is, feature engineering and prediction. The feature engineering aspect is used to address the trend and seasonality issues of time series data. The issues of fitting the model to time series data can also be resolved by it.

Deep learning is used to combine the feature extraction of time series with a nonlinear autoregressive model for higher level prediction. Deep learning is used to extract useful information from the features automatically without using any human effort or complex statistical techniques.

The training data can be collected from gas concentration measurements. The training data can be collected from various environments. For example, gas concentration measurements can take place in power plants. There are currently 1470 generators at 617 facilities in the United States alone that use coal as the major source of energy to generate electricity. Of these facilities, 141 are considered industrial, institutional or commercial sites that consume most of the electricity produced on-site. The remaining 476 sites are identified as "power plants" owned by electric utilities and independent power producers that generate and sell electricity as their primary business. The primary goals that drive these power plants are increasing efficiency and throughput, reducing emissions of pollutants, and maintaining a high level of safety. Obtaining these goals ensures that the power plants generate the highest profits, while complying with environmental regulations and assuring workplace and community safety. An accurate measurement of the carbon monoxide (CO) concentration in the boiler flue gas can be used to achieve the goals of combustion efficiency, pollutant emissions reduction, and safe operation. By measuring the concentration of CO, power plants are able fine tune the air to fuel ratio used on the burners to obtain the highest combustion efficiency. Measuring the CO concentration allows the power plants to reduce the amount combustion air used while ensuring complete combustion, reducing the production of the pollutant NOx.

The training data can be collected from various environments, such as, but not limited to, combustion systems. Combustion occurs when fossil fuels, such as natural gas, fuel oil, coal or gasoline, react with oxygen in the air to produce heat. The heat from burning fossil fuels is used for industrial processes, environmental heating or to expand gases in a cylinder and push a piston. Boilers, furnaces and engines are important users of fossil fuels. Fossil fuels are hydrocarbons, meaning they are composed primarily of carbon and hydrogen. When fossil fuels are burned, carbon dioxide ($CO_2$) and water ($H_2O$) are the principle chemical products, formed from the reactants carbon and hydrogen in the fuel and oxygen ($O_2$) in the air.

Combustion analysis involves the measurement of gas concentrations, temperatures and pressure for boiler tune-ups, emissions checks and safety improvements. Parameters that are commonly examined include: oxygen ($O_2$), carbon monoxide (CO), carbon dioxide ($CO_2$), exhaust gas temperature, supplied combustion air temperature, nitric oxide (NO), nitrogen dioxide ($NO_2$), and sulfur dioxide ($SO_2$). Carbon monoxide, sulfur dioxide, nitrogen oxides and particles are undesirable emissions associated with burning fossil fuels. These compounds are toxic, contribute to acid rain and smog and can ultimately cause respiratory problems.

Therefore, knowing what needs to be predicted will help in deciding which data can be more valuable to collect. In the instant case, the data to be collected can be at least concentration of gas emissions at power plants and combustion parameters. Moreover, when formulating the issue, data exploration can be conducted in view of classification, clustering, regression, and ranking approaches. The training database 416 can be used as a supplement to predict gas concentration emissions or levels or concentrations in other systems. For example, greenhouse gas emissions data collected and stored in the training database 416 can be used to help in predicting gas emissions from automobiles or vehicles.

Figure 5:
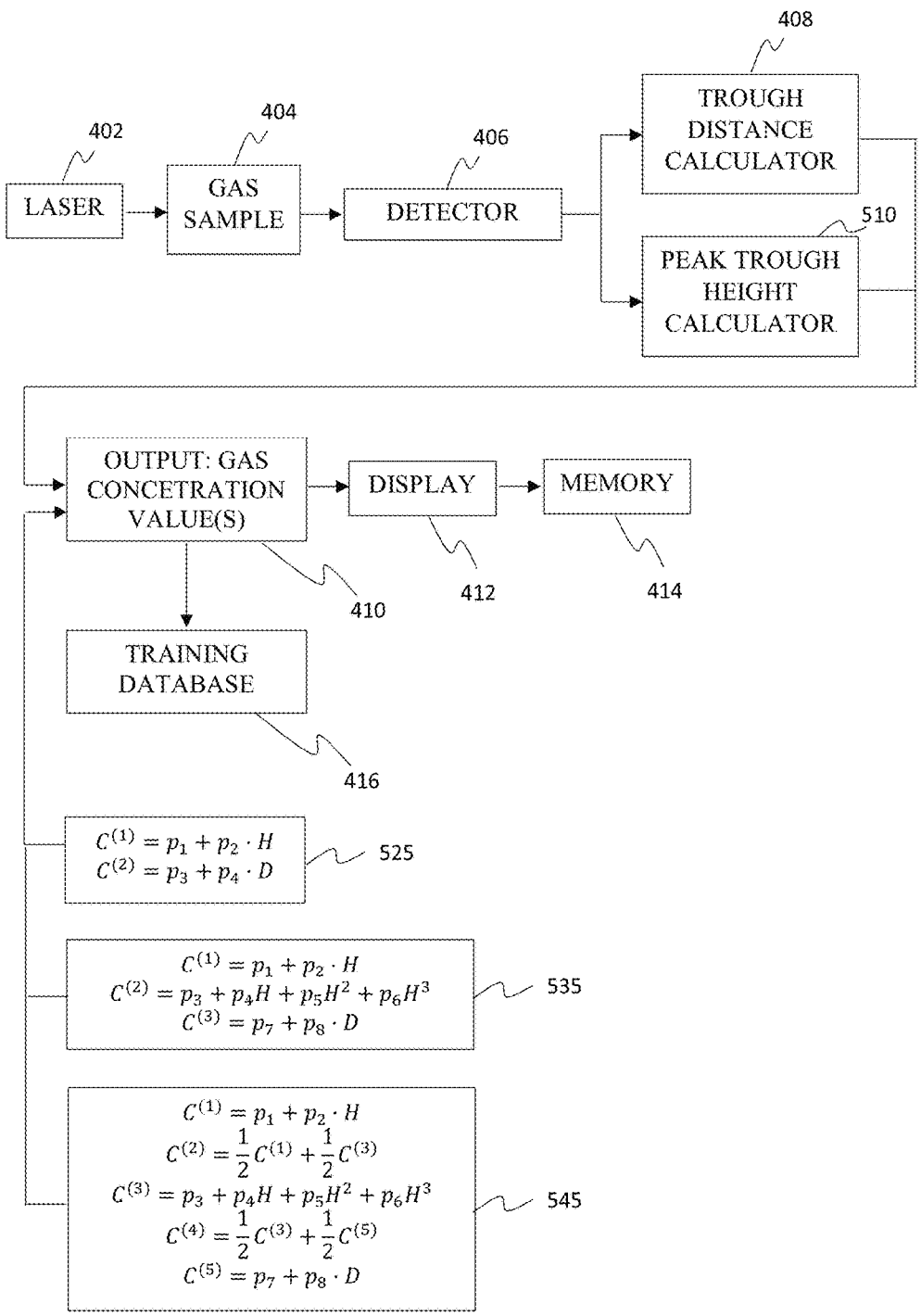
FIG. 5 is an example system for calculating gas concentration values by employing a trough distance calculator and a peak trough height calculator in combination, in accordance with embodiments of the present invention.

FIG. 5 is an example system for calculating gas concentration values by employing a trough distance calculator and a peak trough height calculator, in accordance with embodiments of the present invention.

The system in FIG. 5 is similar to the system in FIG. 4 and a detailed explanation of similar elements will be omitted.

Light emitted from robust, tunable diode sources 402 is passed through a gaseous test sample 404 to a detector 406, and the absorption of light can be related to gas temperature, pressure, species concentration, and velocity using spectral absorption models for the target absorbing species. In some cases, a trough distance calculator 408 and a peak trough height calculator 510 are employed after the detector 406. The trough distance calculator 408 and the peak trough height calculator 510 can be software components.

Thus, the system in FIG. 5 further includes a peak trough height calculator 510 for determining a peak trough height. This peak trough height can be used in combination or in tandem with the trough distance in order to calculate gas concentration values 410. The new generated data can be provided to the training database 416.

In one example, the trough distance (D) and the peak-trough height (H) can be employed to calculate gas concentration (C). The relation between gas concentration C and measured 2f signal (D and H) is divided into two intervals:

C is a linear function of H (525): $C^{(1)}=p_1+p_2 \cdot H$.
C is a linear function of D (525): $C^{(2)}=p_3+p_4 \cdot D$.

There is a threshold value (Th) of D to determine which interval C is in. When C is low enough, D is below Th and H can be considered as linearly related to C. So C is in interval a. Otherwise, C is so high that H is no longer linearly dependent on C, and C is in interval b.

The multi-point calibration process determines Th by measuring D and H at different known concentration C and by setting the Th value at the point between a linear region and a nonlinear region of the optical absorption. The multi-point calibration process can further determine coefficients $p_1$, $p_2$, $p_3$ and $p_4$ by measuring D at different known concentration C.

In use, measure D. If D<Th, then C is in interval a, otherwise C is in interval b. If C is in interval a, calculate C by using measured H and equation a; otherwise, calculate C by using measured D and equation b.

In another example, the trough distance (D) and the peak-trough height (H) can be employed to calculate gas concentration (C). The relation between gas concentration C and measured 2f signal (D and H) is divided into three intervals:

C is a linear function of H (535): $C^{(1)}=p_1+p_2 \cdot H$.
C is a $3^{rd}$ degree polynomial function of H (535): $C^{(2)}=p_3+p_4 H+p_5 H^2+p_6 H^3$.
C is a linear function of D (535): $C^{(3)}=p_7+p_8 \cdot D$.

There are two threshold values (Th1 and Th2) of D to determine which interval C is in. When C is low enough, D is below Th1 and H can be considered as linearly related to C. So C is in interval a. When C is high enough that H is nonlinearly related to C, C is in interval b. When C is very high that H is no longer increasing or even decreasing with C, C is in interval c.

The multi-point calibration process can determine $Th_1$ and $Th_2$ by measuring D and H at different known concentration C and by setting the $Th_1$ value at the point between a linear region, where C and H are approximately linearly related, and a nonlinear region, where the relation between C and H can be approximated by $3^{rd}$ degree polynomial function. The multi-point calibration process can set the $Th_2$ value at the point between the nonlinear region and a saturation region, where C is too high that the $3^{rd}$ degree polynomial function is no long valid. The multi-point calibration process can further determine coefficients $p_1$ to $p_8$ by measuring D at different known concentration C.

In use, measure D. If D<$Th_1$, then C is in interval a. If $Th_1 \leq D < Th_2$, then C is in interval b. If D≥$Th_1$, then C is in interval c.

If C is in interval a, calculate C by using measured H and equation a. If C is in interval b, calculate C by using measured H and equation b. If C is in interval c, calculate C by using measured D and equation c.

In another example, the trough distance (D) and the peak-trough height (H) can be employed to calculate gas concentration (C). The relation between gas concentration C and measured 2f signal (D and H) is divided into five intervals:

C is a linear function of H (545): $C^{(1)}=p_1+p_2 \cdot H$
C is an average of interval a and c (545): $C^{(2)}=\frac{1}{2}C^{(1)}+\frac{1}{2}C^{(3)}$
C is a 3rd degree polynomial function of H (545): $C^{(3)}=p_3+p_4 H+p_5 H^2+p_6 H^3$
C is an average of interval c and e (545): $C^{(4)}=\frac{1}{2}C^{(3)}+\frac{1}{2}C^{(5)}$
C is a linear function of D (545): $C^{(5)}=p_7+p_8 \cdot D$ There are four threshold values ($Th_1$ to $Th_4$) of D to determine which interval C is in. $Th_1$ to $Th_4$ are determined by the evolution and transition points of the relation between C and 2f signal shape, similarly as in examples 1-3 above.

The multi-point calibration process can determine $Th_1$ to $Th_4$ by measuring D and H at different known concentration C and by setting the $Th_1$ through $Th_4$ accordingly. The multi-point calibration process can further determine coefficients $p_1$ to $p_8$ by measuring D at different known concentration C.

In use, measure D. If D<$Th_1$, then C is in interval a. If $Th_1 \leq D < Th_2$, then C is in interval b. If $Th_2 \leq D < Th_3$, then C is in interval c. If $Th_3 \leq D < Th_4$, then C is in interval d. If D≥$Th_4$, then C is in interval e. Use the corresponding equations to calculate C in different intervals.

Figure 6:
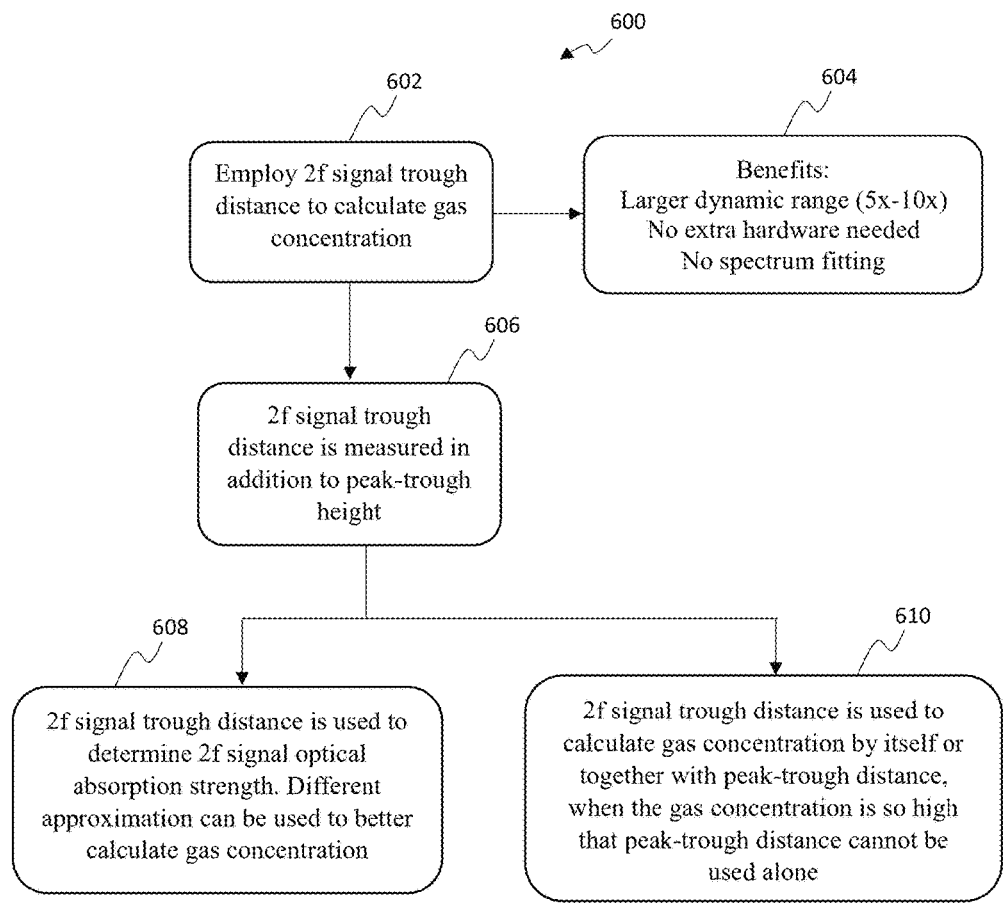
FIG. 6 is an example of the benefits for employing a trough distance calculator to calculate gas concentration, in accordance with embodiments of the present invention.

FIG. 6 is an example of the benefits for employing a trough distance calculator to calculate gas concentration, in accordance with embodiments of the present invention.

At block 602, the methods and systems employ a 2f signal trough distance to calculate gas concentration.

At block 604, the benefits of employing a 2f signal trough distance to calculate gas concentration are, e.g., creating a larger dynamic range (5×-10×), not needing any extra hardware components, and no need for spectrum fitting.

At block 606, in alternative embodiments, the 2f signal trough distance is measured in combination with a peak trough height.

At block 608, the 2f signal trough distance is used to determine 2f signal optical absorption strength. Different approximation can be used to better calculate gas concentration At block 610, 2f signal trough distance is used to calculate gas concentration by itself or together with peak-trough distance, when the gas concentration is so high that peak-trough distance cannot be used alone.

Figure 7:
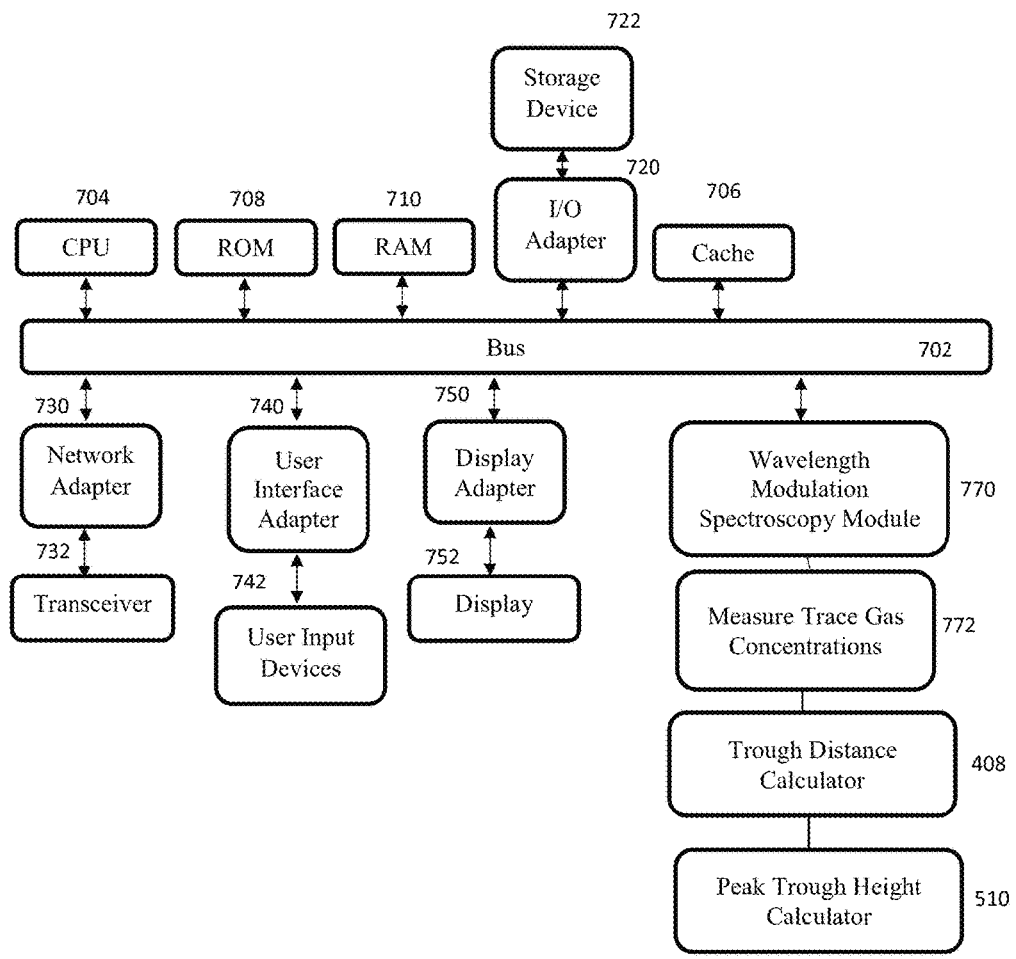
FIG. 7 is block/flow diagram of an exemplary processing system employing a trough distance calculator and a peak trough height calculator, in accordance with embodiments of the present invention.

FIG. 7 is block/flow diagram of an exemplary processing system employing a trough distance calculator and a peak trough height calculator, in accordance with embodiments of the present invention.

The processing system includes at least one processor or processor device (CPU) 704 operatively coupled to other components via a system bus 702. A cache 706, a Read Only Memory (ROM) 708, a Random Access Memory (RAM) 710, an input/output (I/O) adapter 720, a network adapter 730, a user interface adapter 740, and a display adapter 750, are operatively coupled to the system bus 702. A wavelength modulation spectroscopy system or module 770 can be connected to bus 702. The wavelength modulation spectroscopy system or module 770 can be employed to measure trace gas concentrations 772 via a trough distance calculator 408 (FIGS. 4 and 5) and a peak trough height calculator 510 (FIG. 5).

A storage device 722 is operatively coupled to system bus 702 by the I/O adapter 720. The storage device 722 can be any of a disk storage device (e.g., a magnetic or optical disk storage device), a solid state magnetic device, and so forth.

A transceiver 732 is operatively coupled to system bus 702 by network adapter 730.

User input devices 742 are operatively coupled to system bus 702 by user interface adapter 740. The user input devices 742 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 742 can be the same type of user input device or different types of user input devices. The user input devices 742 are used to input and output information to and from the processing system.

A display device 752 is operatively coupled to system bus 702 by display adapter 750.

Of course, the processing system may also include other elements (not shown), as readily contemplated by one of skill in the art, as well as omit certain elements. For example, various other input devices and/or output devices can be included in the system, depending upon the particular implementation of the same, as readily understood by one of ordinary skill in the art. For example, various types of wireless and/or wired input and/or output devices can be used. Moreover, additional processors, processor devices, controllers, memories, and so forth, in various configurations can also be utilized as readily appreciated by one of ordinary skill in the art. These and other variations of the processing system are readily contemplated by one of ordinary skill in the art given the teachings of the present invention provided herein.

Figure 8:
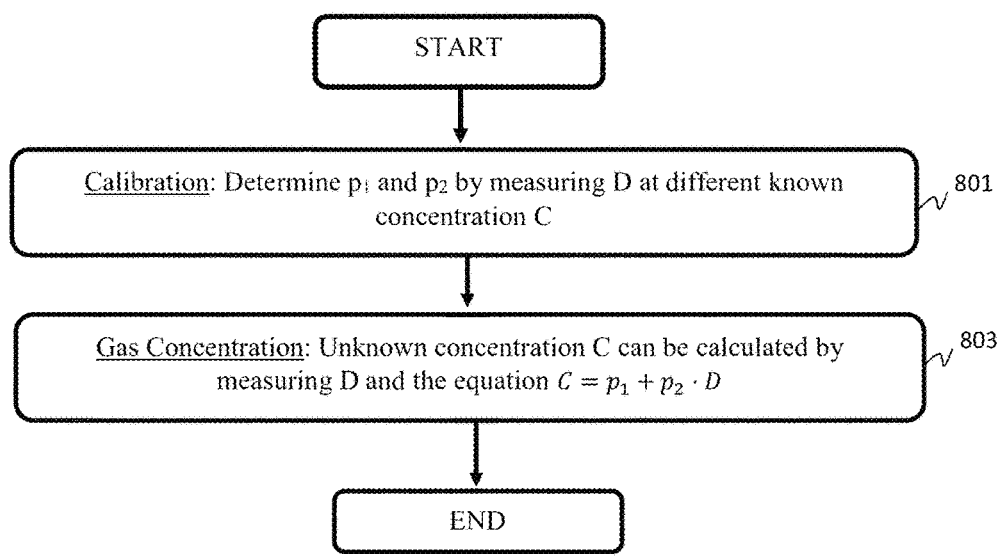
FIG. 8 is block/flow diagram of an exemplary calibration process and method for calculating gas concentration levels by only employing trough distance, in accordance with embodiments of the present invention.

FIG. 8 is block/flow diagram of an exemplary calibration process and method for calculating gas concentration levels by only employing trough distance, in accordance with embodiments of the present invention.

At block 801, determine $p_1$ and $p_2$ by measuring D at different known concentration C.

After the calibration process has been completed, the gas concentration calculation process commences.

At block 803, unknown concentration C can be calculated by measuring D and the equation $C=p_1+p_2 \cdot D$.

Figure 9:
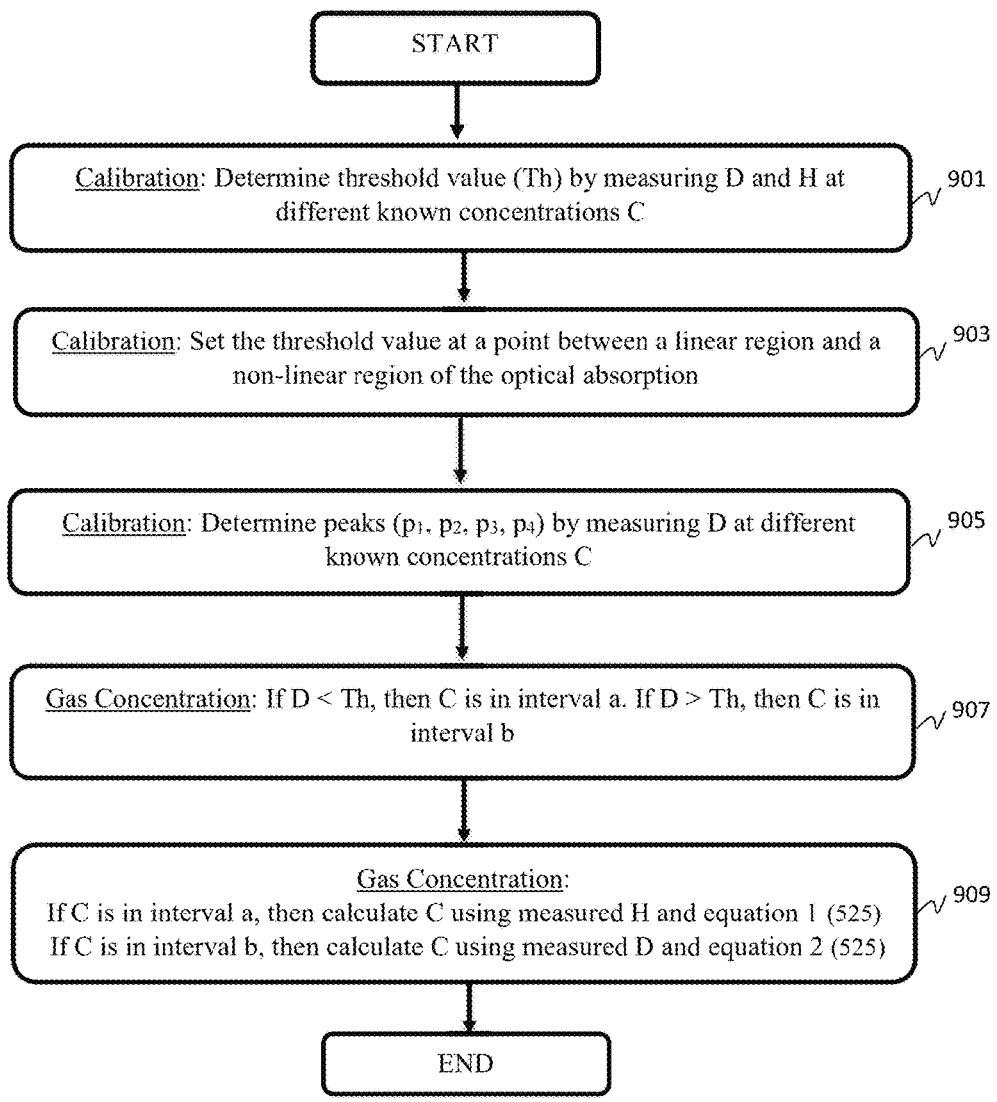
FIG. 9 is block/flow diagram of an exemplary calibration process and method for calculating gas concentration levels by dividing the relation between gas concentration and the measured signal into two intervals, in accordance with embodiments of the present invention.

FIG. 9 is block/flow diagram of an exemplary calibration process and method for calculating gas concentration levels by dividing the relation between gas concentration and the measured signal into two intervals, in accordance with embodiments of the present invention.

Blocks 901, 903, and 905 refer to the calibration process, whereas blocks 907 and 909 refer to the gas concentration calculation process.

At block 901, determine threshold value (Th) by measuring D and H at different known concentrations C.

At block 903, set the threshold value at a point between a linear region and a nonlinear region of the optical absorption.

At block 905, determine coefficients ($p_1$, $p_2$, $p_3$, $p_4$) by measuring D at different known concentrations C.

After the calibration process has been completed, the gas concentration calculation process commences.

At block 907, if D<Th, then C is in interval a. If D>Th, then C is in interval b.

At block 909, if C is in interval a, then calculate C using measured H and equation 1 and if C is in interval b, then calculate C using measured D and equation 2, where equation 1 is given by: $C^{(1)}=p_1+p_2 \cdot H$ and equation 2 is given by: $C^{(2)}=p_3+p_4 \cdot D$.

Figure 10:
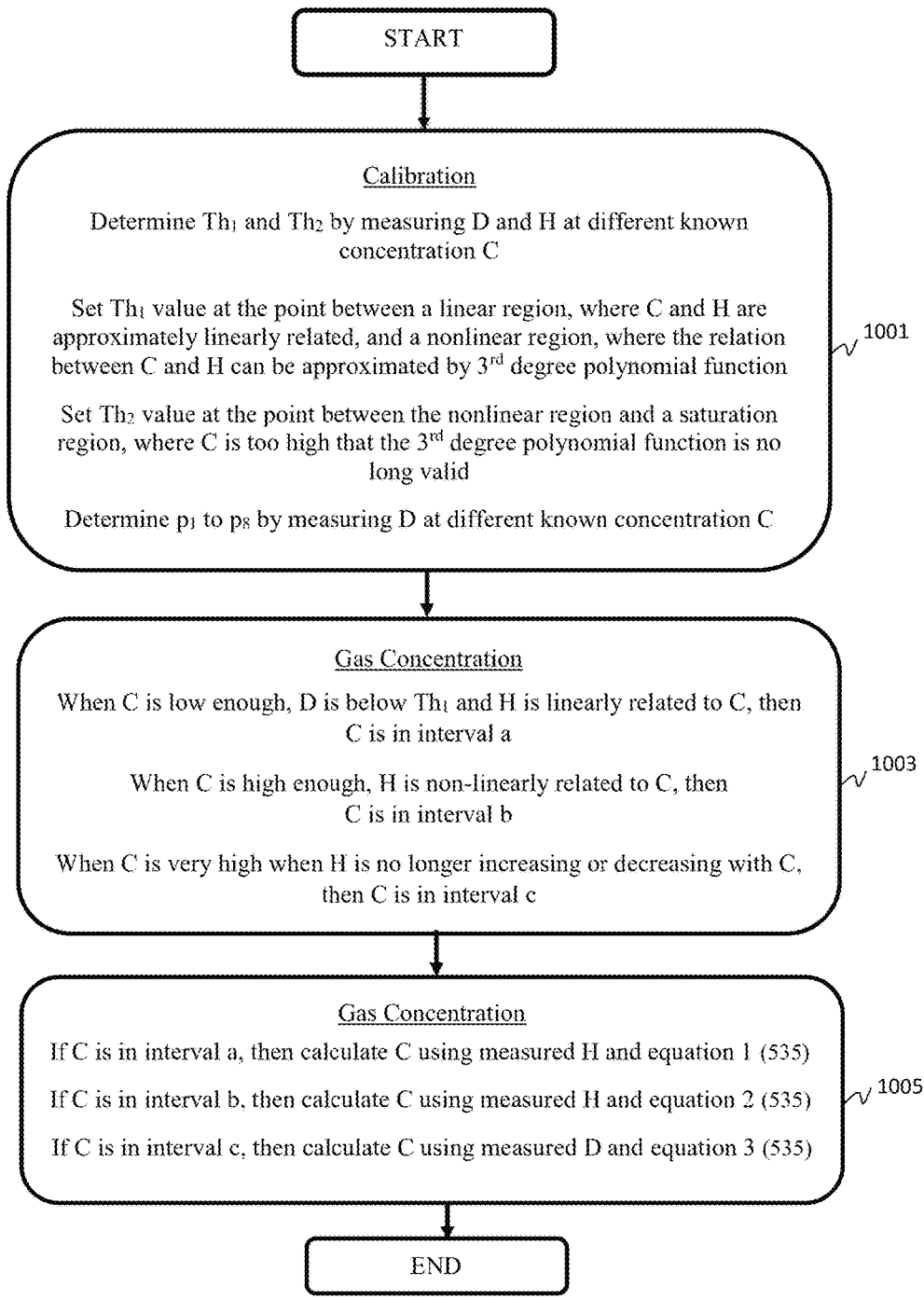
FIG. 10 is block/flow diagram of an exemplary calibration process and method for calculating gas concentration levels by dividing the relation between gas concentration and the measured signal into three intervals, in accordance with embodiments of the present invention.

FIG. 10 is block/flow diagram of an exemplary calibration process and method for calculating gas concentration levels by dividing the relation between gas concentration and the measured signal into three intervals, in accordance with embodiments of the present invention.

Block 1001 refers to the calibration process, whereas blocks 1003 and 1005 refer to the gas concentration calculation process.

At block 1001, determine $Th_1$ and $Th_2$ by measuring D and H at different known concentration C, then set $Th_1$ value at the point between a linear region, where C and H are approximately linearly related, and a nonlinear region, where the relation between C and H can be approximated by $3^{rd}$ degree polynomial function. Next, set $Th_2$ value at the point between the nonlinear region and a saturation region, where C is too high that the $3^{rd}$ degree polynomial function is no long valid. Finally, determine $p_1$ to $p_8$ by measuring D at different known concentration C.

After the calibration process has been completed, the gas concentration calculation process commences.

At block 1003, when C is low enough, D is below $Th_1$ and H is linearly related to C, then C is in interval a. When C is high enough, H is non-linearly related to C, then C is in interval b. When C is very high when H is no longer increasing or decreasing with C, then C is in interval c.

At block 1005, if C is in interval a, then calculate C using measured H and equation 1, if C is in interval b, then calculate C using measured H and equation 2, and if C is in interval c, then calculate C using measured D and equation 3, where equation 1 is given by: $C^{(1)}=p_1+p_2 \cdot H$, where equation 2 is given by: $C^{(2)}=p_3+p_4 H+p_5 H^2+p_6 H^3$, and equation 3 is given by: $C^{(3)}=p_7+p_8 \cdot D$.

Figure 11:
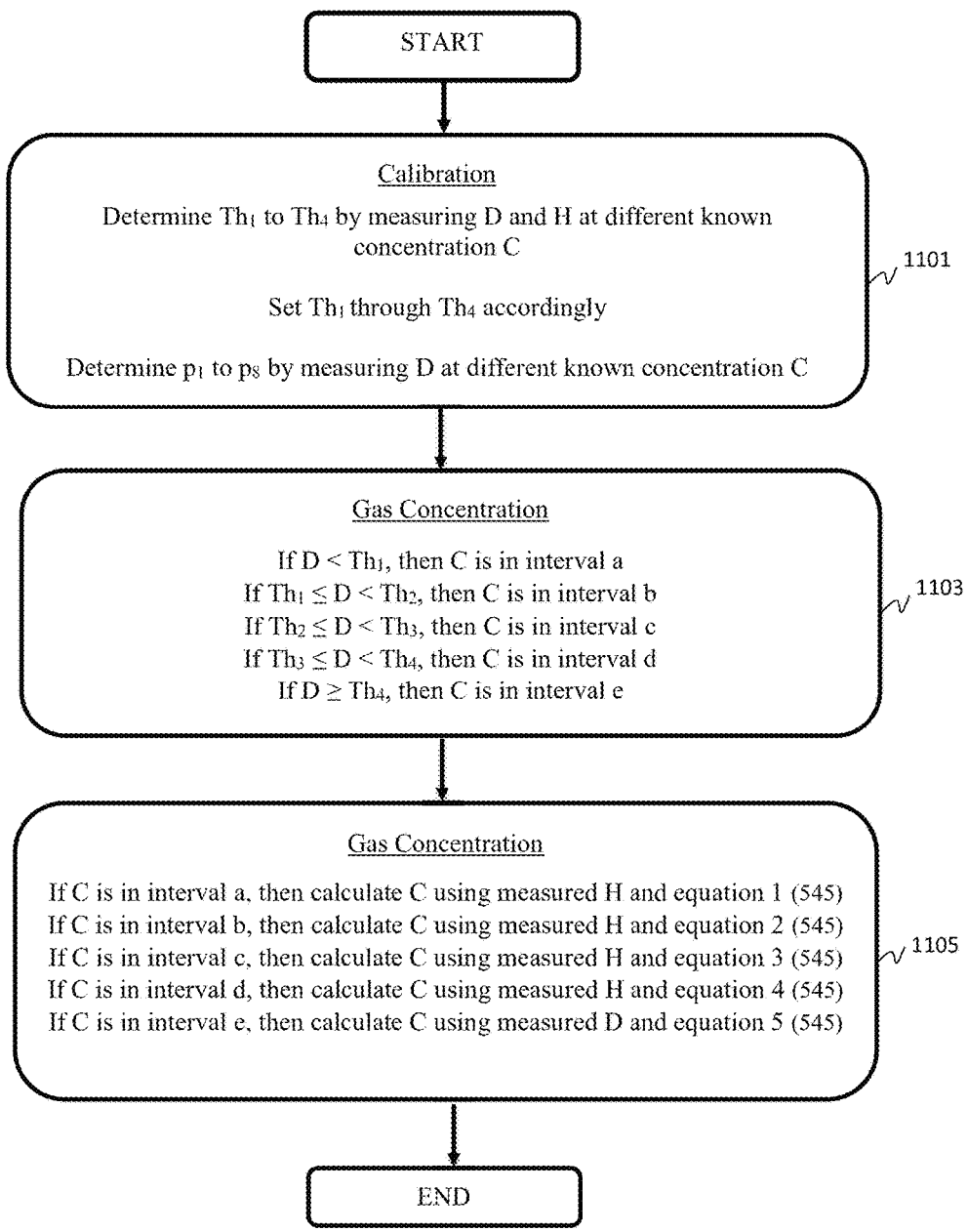
FIG. 11 is block/flow diagram of an exemplary calibration process and method for calculating gas concentration levels by dividing the relation between gas concentration and the measured signal into five intervals, in accordance with embodiments of the present invention.

FIG. 11 is block/flow diagram of an exemplary calibration process and method for calculating gas concentration levels by dividing the relation between gas concentration and the measured signal into five intervals, in accordance with embodiments of the present invention.

Block 1101 refers to the calibration process, whereas blocks 1103 and 1105 refer to the gas concentration calculation process.

At block 1101, determine $Th_1$ to $Th_4$ by measuring D and H at different known concentration C, then set $Th_1$ through $Th_4$ accordingly and determine $p_1$ to $p_8$ by measuring D at different known concentration C.

After the calibration process has been completed, the gas concentration calculation process commences.

At block 1103, if $D<Th_1$, then C is in interval a and if $Th_1 \le D<Th_2$, then C is in interval b. If $Th_2 \le D<Th_3$, then C is in interval c and if $Th_3 \le D<Th_4$, then C is in interval d. If $D \ge Th_4$, then C is in interval e.

At block 1105:

If C is in interval a, then calculate C using measured H and equation 1, where equation 1 is given by: $C^{(1)} = p_1 + p_2 \cdot H$.

If C is in interval b, then calculate C using measured H and equation 2, where equation 2 is given by: $C^{(2)} = \frac{1}{2}C^{(1)} + \frac{1}{2}C^{(3)}$.

If C is in interval c, then calculate C using measured H and equation 3, where equation 3 is given by: $C^{(3)} = p_3 + p_4 H + p_5 H^2 + p_6 H^3$.

If C is in interval d, then calculate C using measured H and equation 4, where equation 4 is given by: $C^{(4)} = \frac{1}{2}C^{(3)} + \frac{1}{2}C^{(5)}$.

If C is in interval e, then calculate C using measured D and equation 5, where equation 5 is given by: $C^{(5)} = p_7 + p_8 \cdot D$.

As used herein, the terms "data," "content," "information" and similar terms can be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, the data can be received directly from the another computing device or can be received indirectly via one or more intermediary computing devices, such as, for example, one or more servers, relays, routers, network access points, base stations, and/or the like. Similarly, where a computing device is described herein to send data to another computing device, the data can be sent directly to the another computing device or can be sent indirectly via one or more intermediary computing devices, such as, for example, one or more servers, relays, routers, network access points, base stations, and/or the like.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," "calculator," "device," or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical data storage device, a magnetic data storage device, or any suitable combination of the foregoing. In the context of this document, a computer readable storage medium may be any tangible medium that can include, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks or modules.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks or modules.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks or modules.

It is to be appreciated that the term "processor" as used herein is intended to include any processing device, such as, for example, one that includes a CPU (central processing unit) and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc. Such memory may be considered a computer readable storage medium.

In addition, the phrase "input/output devices" or "I/O devices" as used herein is intended to include, for example, one or more input devices (e.g., keyboard, mouse, scanner, etc.) for entering data to the processing unit, and/or one or more output devices (e.g., speaker, display, printer, etc.) for presenting results associated with the processing unit.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method executed on a processor for measuring gas concentration from a 2f signal in wavelength modulation spectroscopy, the method comprising:
    emitting a beam of light from a laser to pass through a gas sample;
    calculating a gas measurement value from the gas sample via a trough distance calculator using a trough distance of a gas absorption line's 2f signal;
    calibrating the gas measurement value via a multi-point calibration process; and
    outputting the gas measurement value to a user interface of a computing device;
    wherein the gas concentration is a linear function of trough distance, the gas concentration given by $C=p_1+p_2 \cdot D$, where C is gas concentration, D is trough distance, and $p_1$, $p_2$ are coefficients.

2. The method of claim 1, wherein the gas measurement value determined from calculating the trough distance is provided to a training database to be used as training data.

3. The method of claim 1, wherein the 2f signal trough distance is further employed to determine optical absorption strength of the 2f signal.

4. A computer-implemented method executed on a processor for measuring gas concentration from a 2f signal in wavelength modulation spectroscopy, the method comprising:
    emitting a beam of light from a laser to pass through a gas sample;
    calculating a gas measurement value from the gas sample via a trough distance calculator using a trough distance of a gas absorption line's 2f signal;
    calibrating the gas measurement value via a multi-point calibration process; and
    outputting the gas measurement value to a user interface of a computing device;
    wherein the gas measurement value is calculated by employing a peak trough height in combination with the trough distance, the peak trough height calculated from a peak trough height calculator; and
    wherein the gas concentration is a linear function of the peak trough height and a linear function of the trough distance, the concentration given by $C^{(1)}=p_1+p_2 \cdot H$ and by $C^{(2)}=p_3+p_4 \cdot D$, where C is gas concentration, D is trough distance, H is peak trough height, and $p_1$-$p_4$ are coefficients.

5. A computer-implemented method executed on a processor for measuring gas concentration from a 2f signal in wavelength modulation spectroscopy, the method comprising:
    emitting a beam of light from a laser to pass through a gas sample;
    calculating a gas measurement value from the gas sample via a trough distance calculator using a trough distance of a gas absorption line's 2f signal;
    calibrating the gas measurement value via a multi-point calibration process; and
    outputting the gas measurement value to a user interface of a computing device;
    wherein the gas measurement value is calculated by employing a peak trough height in combination with the trough distance, the peak trough height calculated from a peak trough height calculator; and
    wherein the gas concentration is a linear function of the peak trough height, a $3^{rd}$ degree polynomial function of the peak trough height, and a linear function of the trough distance, the concentration given by $C^{(1)}=p_1+$ $p_2 \cdot H$, $C^{(2)}=p_3+p_4H+p_5H^2+p_6H^3$, and $C^{(3)}=p_7+p_8 \cdot D$, where C is gas concentration, D is trough distance, H is peak trough height, and $p_1$-$p_8$ are coefficients.

6. A computer-implemented method executed on a processor for measuring gas concentration from a 2f signal in wavelength modulation spectroscopy, the method comprising:
   emitting a beam of light from a laser to pass through a gas sample;
   calculating a gas measurement value from the gas sample via a trough distance calculator using a trough distance of a gas absorption line's 2f signal;
   calibrating the gas measurement value via a multi-point calibration process; and
   outputting the gas measurement value to a user interface of a computing device;
   wherein the gas measurement value is calculated by employing a peak trough height in combination with the trough distance, the peak trough height calculated from a peak trough height calculator; and
   wherein the gas concentration is a linear function of the peak trough height, an average of two intervals, a $3^{rd}$ degree polynomial function of the peak trough height, an average of two other intervals, and a linear function of the trough distance, the concentration given by $C^{(1)}=p_1+p_2 \cdot H$, $C^{(2)}=\frac{1}{2}C^{(1)}+\frac{1}{2}C^{(3)}$, $C^{(3)}=p_3+p_4H+p_5H^2+p_6H^3$, $C^{(4)}=\frac{1}{2}C^{(3)}+\frac{1}{2}C^{(5)}$, and $C^{(5)}=p_7+p_8 \cdot D$, where C is gas concentration, D is trough distance, H is peak trough height, and $p_1$-$p_8$ are coefficients.

7. A non-transitory computer-readable storage medium comprising a computer-readable program for measuring gas concentration from a 2f signal in wavelength modulation spectroscopy, wherein the computer-readable program when executed on a computer causes the computer to perform the steps of:
   emitting a beam of light from a laser to pass through a gas sample;
   calculating a gas measurement value from the gas sample via a trough distance calculator using a trough distance of a gas absorption line's 2f signal;
   calibrating the gas measurement value via a multi-point calibration process; and
   outputting the gas measurement value to a user interface of a computing device;
   wherein the gas concentration is a linear function of trough distance, the gas concentration given by $C=p_1+p_2 \cdot D$, where C is gas concentration, D is trough distance, and $p_1$, $p_2$ are coefficients.

8. The non-transitory computer-readable storage medium of claim 7, wherein the gas measurement value determined from calculating the trough distance is provided to a training database to be used as training data.

9. The non-transitory computer-readable storage medium of claim 7, wherein the 2f signal trough distance is further employed to determine optical absorption strength of the 2f signal.

10. A non-transitory computer-readable storage medium comprising a computer-readable program for measuring gas concentration from a 2f signal in wavelength modulation spectroscopy, wherein the computer-readable program when executed on a computer causes the computer to perform the steps of:
   emitting a beam of light from a laser to pass through a gas sample;
   calculating a gas measurement value from the gas sample via a trough distance calculator using a trough distance of a gas absorption line's 2f signal;
   calibrating the gas measurement value via a multi-point calibration process; and
   outputting the gas measurement value to a user interface of a computing device;
   wherein the gas measurement value is calculated by employing a peak trough height in combination with the trough distance, the peak trough height calculated from a peak trough height calculator; and
   wherein the gas concentration is a linear function of the peak trough height and a linear function of the trough distance, the concentration given by $C^{(1)}=p_1+p_2 \cdot H$ and by $C^{(2)}=p_3+p_4 \cdot D$, where C is gas concentration, D is trough distance, H is peak trough height, and $p_1$-$p_4$ are coefficients.

11. A non-transitory computer-readable storage medium comprising a computer-readable program for measuring gas concentration from a 2f signal in wavelength modulation spectroscopy, wherein the computer-readable program when executed on a computer causes the computer to perform the steps of:
   emitting a beam of light from a laser to pass through a gas sample;
   calculating a gas measurement value from the gas sample via a trough distance calculator using a trough distance of a gas absorption line's 2f signal;
   calibrating the gas measurement value via a multi-point calibration process; and
   outputting the gas measurement value to a user interface of a computing device;
   wherein the gas measurement value is calculated by employing a peak trough height in combination with the trough distance, the peak trough height calculated from a peak trough height calculator; and
   wherein the gas concentration is a linear function of the peak trough height, a $3^{rd}$ degree polynomial function of the peak trough height, and a linear function of the trough distance, the concentration given by $C^{(1)}=p_1+p_2 \cdot H$, $C^{(2)}=p_3+p_4H+p_5H^2+p_6H^3$, and $C^{(3)}=p_7+p_8 \cdot D$, where C is gas concentration, D is trough distance, H is peak trough height, and $p_1$-$p_8$ are coefficients.

12. A non-transitory computer-readable storage medium comprising a computer-readable program for measuring gas concentration from a 2f signal in wavelength modulation spectroscopy, wherein the computer-readable program when executed on a computer causes the computer to perform the steps of:
   emitting a beam of light from a laser to pass through a gas sample;
   calculating a gas measurement value from the gas sample via a trough distance calculator using a trough distance of a gas absorption line's 2f signal;
   calibrating the gas measurement value via a multi-point calibration process; and
   outputting the gas measurement value to a user interface of a computing device;
   wherein the gas measurement value is calculated by employing a peak trough height in combination with the trough distance, the peak trough height calculated from a peak trough height calculator; and
   wherein the gas concentration is a linear function of the peak trough height, an average of two intervals, a $3^{rd}$ degree polynomial function of the peak trough height, an average of two other intervals, and a linear function of the trough distance, the concentration given by $C^{(1)}=p_1+p_2 \cdot H$, $C^{(2)}=\frac{1}{2}C^{(1)}+\frac{1}{2}C^{(3)}$, $C^{(3)}=p_3+p_4H+p_5H^2+p_6H^3$, $C^{(4)}=\frac{1}{2}C^{(3)}+\frac{1}{2}C^{(5)}$, and $C^{(5)}=p_7+p_8 \cdot D$, where C is gas concentration, D is trough distance, H is peak trough height, and $p_1$-$p_8$ are coefficients.

13. A system for measuring gas concentration from a 2f signal in wavelength modulation spectroscopy, the system comprising:
   a laser to emit a beam of light to pass through a gas sample;
   a gas measurement value calculated from the gas sample via a trough distance calculator using a trough distance of a gas absorption line's 2f signal;
   a multi-point calibration system to calibrate the gas measurement value; and
   a user interface of a computing device to output the gas measurement value;
wherein the gas concentration is a linear function of trough distance, the gas concentration given by $C=p_1+p_2 \cdot D$, where C is gas concentration, D is trough distance, and $p_1$, $p_2$ are coefficients.

14. A system for measuring gas concentration from a 2f signal in wavelength modulation spectroscopy, the system comprising:
   a laser to emit a beam of light to pass through a gas sample;
   a gas measurement value calculated from the gas sample via a trough distance calculator using a trough distance of a gas absorption line's 2f signal;
   a multi-point calibration system to calibrate the gas measurement value; and
   a user interface of a computing device to output the gas measurement value;
wherein the gas measurement value is calculated by employing a peak trough height in combination with the trough distance, the peak trough height calculated from a peak trough height calculator; and
wherein the gas concentration is a linear function of the peak trough height and a linear function of the trough distance, the concentration given by $C^{(1)}=p_1+p_2 \cdot H$ and by $C^{(2)}=p_3+p_4 \cdot D$, where C is gas concentration, D is trough distance, H is peak trough height, and $p_1$-$p_4$ are coefficients.

* * * * *